United States Patent [19]

Suga

[11] Patent Number: 4,717,259

[45] Date of Patent: Jan. 5, 1988

[54] LUSTER RATING METHOD AND APPARATUS

[76] Inventor: Shigeru Suga, 4-14 Shinjuku 5-chome, Shinjuku-ku, Tokyo, Japan

[21] Appl. No.: 714,492

[22] Filed: Mar. 21, 1985

[30] Foreign Application Priority Data

May 2, 1983 [JP] Japan ................................. 58-76194

[51] Int. Cl.$^4$ ........................................... G01N 21/47
[52] U.S. Cl. ..................................................... 356/446
[58] Field of Search ............................... 356/445, 446

[56] References Cited

U.S. PATENT DOCUMENTS 2,830,490  4/1958  Pellegrini ............................ 356/446
3,396,627  8/1968  Rouy et al. ......................... 356/446

OTHER PUBLICATIONS

Gardner Laboratory, "Instruments and Methods for Determining Gloss Surface Texture, Sharpness of Reflected Images and Bloom", 1936; 356–446.

Primary Examiner—R. A. Rosenberger
Attorney, Agent, or Firm—Wenderoth, Lind & Ponack

[57] ABSTRACT

A method and apparatus for determining the luster of a surface as a numerical value. The apparatus projects light from a light source through a light diffusing layer and through a layer of semitransparent material having thereon groups of parallel lines for projecting the lines onto the surface of a sample the luster of which is to be determined. The lines projected onto the surface are viewed with the eyes and the degree of distortion among the lines in the respective groups, which occurs due to the various conditions of the surface which affect the luster thereof, and to which has previously been assigned a numerical value, is determined, the numerical value of the thus determined degree of distortion for one group of figures being for the degree of gloss of the surface and the numerical value of the thus determined degree of distortion for another group being for the degree of clarity of the surface. The surface is also visually compared with a scale of predetermined lightness values having preassigned numerical values for determining the closest lightness value, and a lightness coefficient is derived from this lightness value. The sum of the gloss value and the clarity value is multiplied by the lightness coefficient for obtaining a numerical value for the luster of the surface of the sample.

4 Claims, 10 Drawing Figures

FIG. 1.
PRIOR ART
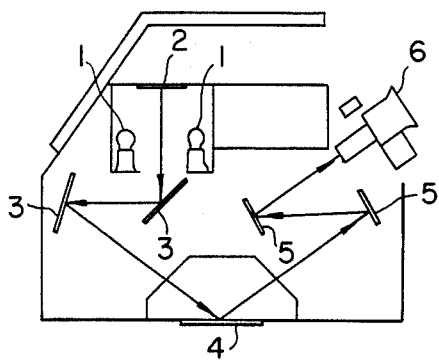
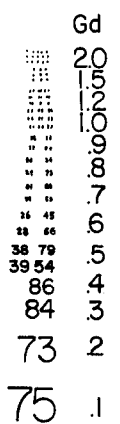
FIG. 2.
FIG. 3.
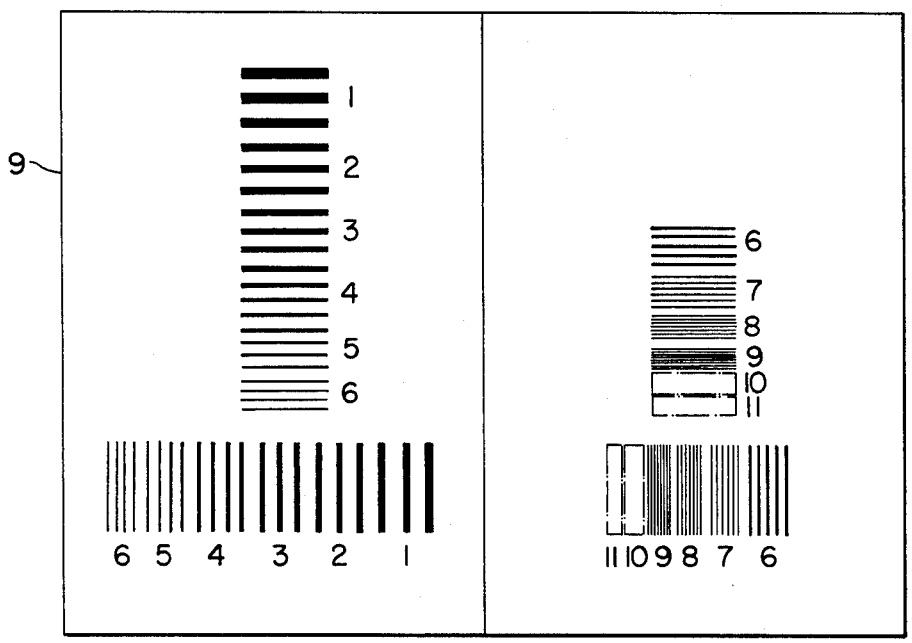
FIG. 4.
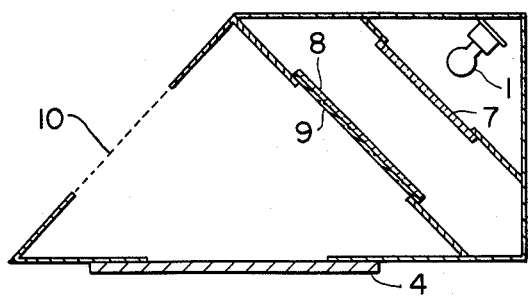

LUSTER RATING METHOD AND APPARATUS

BACKGROUND OF THE INVENTION

1. Field of the Invention

This invention relates to a method and apparatus for rating in numerical values the luster of the surface of a painted plate, an anodic oxidation film-carrying aluminum plate and lacquer ware.

2. Description of the Prior Art

It is considered that the luster of a surface can be rated by degrees, which are determined by the human eye, of the gloss, clarity, or distinctness or sharpness of image as it is sometimes called, and lightness, the three optical factors, of the surface. Devices for determining and displaying the degrees of these three optical factors independently have been developed, but a method of and a device for synthesizing the three factors of the luster of the surface of an object to rate the luster thereof are not available.

The gloss is related to the intensity of the specularly reflected light, which is determined as mirror surface gloss, or specular gloss, by a conventional gloss meter. However, mirror surface gloss does not correspond exactly with visual gloss.

The clarity of the surface of an object is rated in accordance with the image reflecting capability thereof, i.e. the degree of distortion of an image reflected therein. There is a conventional method of optically determining the image reflecting capability of a surface, JISH 8686 "Test Method for the Image Clarity of Anodic Oxidation Coatings of Aluminum and Aluminum Alloy", but this is a method of determining only the image reflecting capability of a surface.

In case of, for example, an anodic oxidation film, an extremely thin, nearly semitransparent outer layer exists on the outer surface thereof. The outer surface as a whole of this film looks misty even when it has high degrees of gloss and visibility. Thus, the brightness, which is an optical factor other than the gloss and visibility, of a surface has an influence upon the luster thereof.

As described above, these three optical factors have different characteristics. However, when the surface of an object is observed with the naked eye, the degrees of the three optical factors thereof are sensed simultaneously and determined collectively as the luster thereof. A method of visually determining the luster of a surface has not yet become available. Therefore, there has been no choice, up to now, but to determine and display the degrees of the three optical factors of a surface separately.

A method of displaying the luster of a surface rationally so that the luster value displayed agrees with that determined visually has not yet become available. A general-use apparatus for visually determining the luster of the surface of an object and the problems of such apparatus will now be described. FIG. 1 is a diagram of the construction of a conventional apparatus of this kind. The figure of a test pattern 2 illuminated directly by two lamps 1 is reflected twice on two mirrors 3 and is then projected onto a sample 4. The figure of the test pattern 2 is shown in FIG. 2. The figure consists of arbitrary numerals of 13 sizes graduated as 0.1, 0.2, ... 1.0, 1.2, 1.5, 2.0. When this test pattern is projected on the sample 4, the image of the figure varies depending upon the condition of the surface of the sample. If the surface on which the test pattern is projected is a perfect mirror surface, even the smallest numeral in the projected image is reflected clearly without any shaded portions and distorted lines. Even a coated surface and an evaporated surface which are finished by highly-advanced techniques usually have minute projections and recesses and gently-waved portions, which cause the projected image to be distorted. In order to determine by this apparatus the degree of luster of a coated surface of an industrial product, for example, an automobile, a standard degree of smoothness of a finished surface is set, and a numerical value corresponding to this standard degree of smoothness is determined as a Gd value. The luster of a coated surface is judged in accordance with this Gd value, as to whether it meets the standard or not.

A method of determining the degree of luster of a coated surface will now be described. The image projected on the sample 4 in FIG. 1 is reflected twice on two mirrors 5. A graduation (Gd value) corresponding to a numeral which can be read through an ocular cylinder 6 is read. The results of judgements of degree of luster made by this conventional apparatus have a low reproducibility and a low accuracy, and differ greatly depending upon the persons who operate the apparatus.

The inventor of the present invention, before developing a luster rating method, considered the causes of the drawbacks encountered in the above conventional method and apparatus, taking into consideration the importance of the gloss and clarity (image reflecting capability) of a surface, which constitute the luster thereof.

The first cause resides in the fact that the test pattern consists of numerals which are not regularly-shaped but irregularlyshaped. Therefore, some numerals can be read and some can not, even when all of these numerals have the same size and represent the same graduation of luster. In some cases, a numeral is read favourably by mistake as some other similarly-shaped numeral. For example, the numbers 8, 9 and 3, the numbers 7, 4 and 1, and the numbers 3 and 5 have somewhat similar shapes, so that they are apt to be mistaken for one another. Since a numeral consists of straight and curved lines of various thicknesses and lengths, the visual power of an examiner has a great influence upon the results of a luster determining operation. This constitutes a cause of the occurrence of great differences among the judgements made by different persons of the luster of a surface.

The second cause resides in the fact that the surface of a sample has directional properties. For example, a plate of Alumite containing aluminum as a base has some orientation of its surface due to the rolling step to which the plate was subjected during manufacture, and a coated plate also has some orientation due to the coating step to which it was subjected during manufacture. Thus, the surfaces of materials generally have orientation in the longitudinal and lateral directions thereof. A test pattern consisting of numerals is composed of a combination of lines which extend in an extremely complicated manner in the longitudinal and lateral directions, such as inclined lines, curved lines and waved lines. Therefore, when test patterns of this type are projected on mirrors to examine the reflecting capability of the surfaces of the patterns, different results are obtained due to the different directional properties of the finished surfaces even if the surfaces look identical.

The third cause resides in the system for illuminating a pattern directly by two lamps as shown in FIG. 1. Due to this illuminating system, the direct light from the lamps is mixed in the projecting light, so that it is often difficult to judge the degree of luster of a surface having a high degree of gloss.

The fourth cause resides in the use of four mirrors. Let the image reflecting capability of a perfect mirror surface be 100%. The actual image reflecting capability of the mirrors used in this type apparatus, since they are obviously not perfect, is not more than 90%. When four such mirrors are used, the drawbacks thereof are necessarily cumulative. Consequently, the grade of clarity given to a sample is lower than the actual grade thereof.

In the light of the above problems, it will be understood clearly that a conventional luster rating method and apparatus is not capable of properly indicating the clarity (image reflecting capability) of a surface.

SUMMARY OF THE INVENTION

An object of the present invention is to provide a novel method of and a novel apparatus for determining accurately the degrees of gloss and clarity of a surface, which constitute the data essential to the rating of the luster thereof.

The above and other objects as well as advantageous features of the invention will become apparent from the following description of the preferred embodiment taken in conjunction with the accompanying drawings.

BRIEF DESCRIPTION OF THE DRAWINGS

FIG. 1 is a diagrammatic sectional view of a conventional luster rating apparatus;

FIG. 2 illustrates a test pattern used in the conventional apparatus;

FIG. 3 shows a chart scale used in the present invention;

FIG. 4 is a sectional elevation of an apparatus according to the present invention;

FIG. 5-1 is a graph showing the relation between the values obtained by the JIS method of determining the image reflecting capability of a surface and those obtained by a conventional method of determining the image reflecting capability of the same surface;

FIG. 5-2 is a graph showing the relation between the values obtained from the same surface by the JIS method of determining the image reflecting capability of a surface and the values of the image reflecting capability obtained by the luster rating method according to the present invention;

DESCRIPTION OF THE PREFERRED EMBODIMENT

Figures 1, 5:
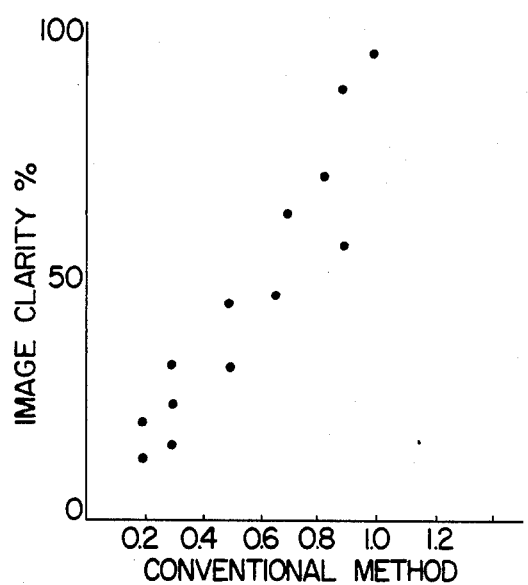

FIG. 3 shows an example of a chart scale used in the present invention. This chart scale consists of the same figures arranged longitudinally and laterally. Each of the longitudinal and lateral scale members, is a group of successive sets of spaced parallel black lines having clear spaces therebetween and having gradually reduced thicknesses are arranged with adjacent black lines in each set spaced by white or clear spaces of the same thickness. The thickness of the lines in the sets are in an arithmetic series of thicknesses of 2.0 mm, 1.75 mm, 1.5 mm, 1.25 mm, 1.0 mm, 0.75 mm, and 0.5 mm. The sets of black lines and spaces of not more than 0.5 mm in thickness, which are used for samples having a high image reflecting capability, have thicknesses of 0.5 mm, 0.25 mm and 0.125 mm. Sets of black lines and spaces of average thicknesses of 0.375 mm and 0.188 mm are added to these sets of lines in the geometric series of thicknesses, and all of them are arranged in the order of thickness, i.e. in sets of lines with 0.5 mm, 0.375 mm, 0.25 mm, 0.188 mm and 0.125 mm thickness. Thus, a combination of simple figures consisting of parallel and regularly-spaced black lines with spaces therebetween is made. The sets are then given arbritary grade numbers, e.g. 1 to 11.

An apparatus developed by the inventor of the present invention and used to rate gloss and clarity of samples by using this chart scale is shown in FIG. 4. The light from an illuminating lamp 1 mounted in a housing 11 reaches a chart scale 9 through first and second diffusion layers 7 and 8. The first diffusion layer 7 consists of a single plate of frosted glass mounted in an aperture in interior partition 7a, and the second diffusion layer 8 is a semitransparent film, i.e. a flim having a haziness value of not less than 90% mounted in an aperture in interior partition 7b, the apertures being aligned with lamp 1. The chart scale 9 is a film on which black lines are printed, or a polished glass plate on which black lines are placed by evaporation of metal thereonto. The chart scale 9 is put on the second diffusion layer 8. The light passing through the chart scale 9 is projected 11 through aperture 4a in the bottom wall of the housing on the axis of the apertures and lamp 1. The reflected image is reflected to aperture 10 which is on the axis of the image reflected from the sample 4.

In this apparatus, the chart scale is projected on the surface of the sample by the nearly perfect diffused light, so that the error caused by the direct light from the lamp in the apparatus used in a conventional method does not occur. According to the apparatus used in the present invention, in which the whole figure on the chart scale is projected uniformly over all parts of the surface of a sample owing to the double diffusion effect, there is no possibility of the figure being erroneously observed. Moreover, because mirrors are not used in this apparatus, no errors occur in the determination of the image reflecting capability of the surface of a sample due to imperfect reflection from such mirrors. Since the chart scale consists of longitudinal and lateral figures of the same shape and size, the luster of the surface of a sample can be rated numerically by using any of these figures. This enables the problem of the directional properties of a surface to be overcome. As may be understood from the drawing, the apparatus has a wide visual field, so that an object surface can be observed easily without fatiguing the eyes. The apparatus can thus be operated simply and manufactured at a very low cost and is light as well as giving excellent performance.

The luster rating method according to the present invention will now be described.

The degrees of gloss and clarity of an object surface are determined with the above-mentioned chart scale and apparatus, and the degree of the lightness of the same is determined by the use of an additionally-prepared lightness scale. The luster of the surface is then rated numerically with the numerical values thus obtained. The important points having a direct relation with this method will now be described.

Figure 6:
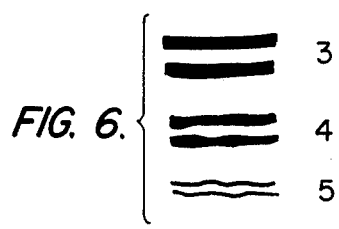
FIG. 6 is a drawing for use in describing how to rate the luster of a surface.

(1) The gloss of the surface of a sample is connected with the intensity of the light specularly reflected therefrom. When light is diffused due to the minute projections and recesses on and in the surface, the intensity of the specularly reflected light from and the gloss of the surface decrease. The unevenness of the thicknesses of the black lines of the chart scale as reflected from the sample in apparatus used in the present invention is read on the graduated thickness lines on the scale, and the gloss of the object surface is rated according to where the unevenness of the thickness of the lines starts to occur, since the degree of unevenness of the thickness of the black lines is related to the intensity of the diffused light. On a surface (for example, a coated surface) having a degree of gloss so high that is nearly equal to that of the gloss of a mirror surface, even thin, black, parallel lines are reflected therein as parallel lines but, in a general coated surface, the boundary between the clear spaces and black lines of Grade 3 thickness looks straight, while the boundary between the clear spaces and black lines of Grade 4 thickness looks distorted, as shown in FIG. 6. In this case, where the boundary between the clear spaces and black lines of Grade 3 thickness looks straight and that between the clear spaces and black lines of Grade 4 thickness appears distorted, the numerical value representing the degree of gloss of the surface is 3. The sum or the average of the numerical values obtained from the longitudinal and lateral chart scale members in accordance with the above-described method is taken as the numerical value representing the degree of gloss of the surface examinated.

Figure 7:
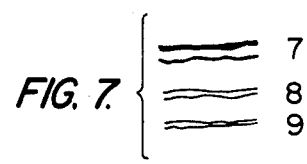
FIG. 7 is a drawing for use in describing how to rate the visibility of a surface.

(2) The clarity of a surface of a sample is determined in accordance with the degree of distortion of an image projected thereon, the occurrence of distortion of such an image being thought to be due to the comparatively large wavy portions, projections and recesses of, on and in the same surface. As shown in FIG. 7, the smaller the thicknesses of the lines in the reflected image of the chart scale, the more difficult it becomes to distinguish the existence of a space between two adjacent black lines, which for Grade 9 even look as if they crossed each other. Since Grade 8 is the lowest grade on the chart scale at which the black lines in a reflected image can be recognized as separate lines, the numerical value representing the clarity of this surface is determined to be 8. The sum or the average of the numerical values obtained from the longitudinal and lateral chart scale members in accordance with the above-described method is used as the numerical value representing the degree of the clarity of the surface examined. The degree of clarity value is a numerical value which can be determined by the chart scale and apparatus of the present invention and which is rational and not influenced by the directional properties of a surface.

Figure 8:
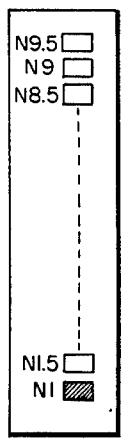
FIG. 8 is a lightness scale.

(3) The lightness of a surface is determined in accordance with the degree of influence of the lightness (for example, a white or black color) of the surface upon the reflection of an image projected thereon. The degree of luster of a surface having a higher visual lightness is judged to be higher than that of the luster of a surface having a lower visual lightness even when the inferior limit value on the chart scale, i.e. the grade at which the black lines in a reflected image of the chart scale can be recognized in a normal state, with respect to these surfaces, and the distortion of such black lines with respect to the same surfaces are in the same grades. The thus determined lightness of a surface is considered to be an important characteristics of solid and metallic coating materials, especially, in the industrial world of automobiles, and has given rise to an important problem in the production of building materials, furniture and ornaments which are surface-treated with an anodic oxidation film. According to the method of the present invention of rating the luster, which includes a lightness component, of a surface by using the above-described apparatus, the lightness of the black lines on the chart scale reflected in the surface of a sample is compared with the color chips N on the lightness scale (set forth in JIS 8721 "Specification of Colors According to Their Three Atributes") shown in FIG. 8, and the symbol shown to one side of the color chip the lightness of which is equal to that of the black lines described above is taken as the lightness. For example, black lines reflected very dark on a flat black-coated plate, and seen as lines the lightness of which is identical to that of the color chip N2 on the lightness scale, are considered to have a lightness of N2, while black lines reflected from a flat white-coated plate surface are lighter and are seen as lines the lightness (gray) of which corresponds to that of the color chip N6, are considered to have a lightness of N6.

The lightness, which is rated according to the lightness scale, of the black lines reflected in the surface of a sample constitutes a factor in the determination of the ease of and difficulty in observing a reflected figure which is rated with respect to the degree of gloss and clarity thereof. Accordingly, when the sum of the numerical values of the grades representative of the gloss and clarity determined by the chart scale of an object surface are multiplied by a coefficient as determined by the lightness of the surface, a value highly correlated with the visual luster thereof can be obtained.

Figure 9:
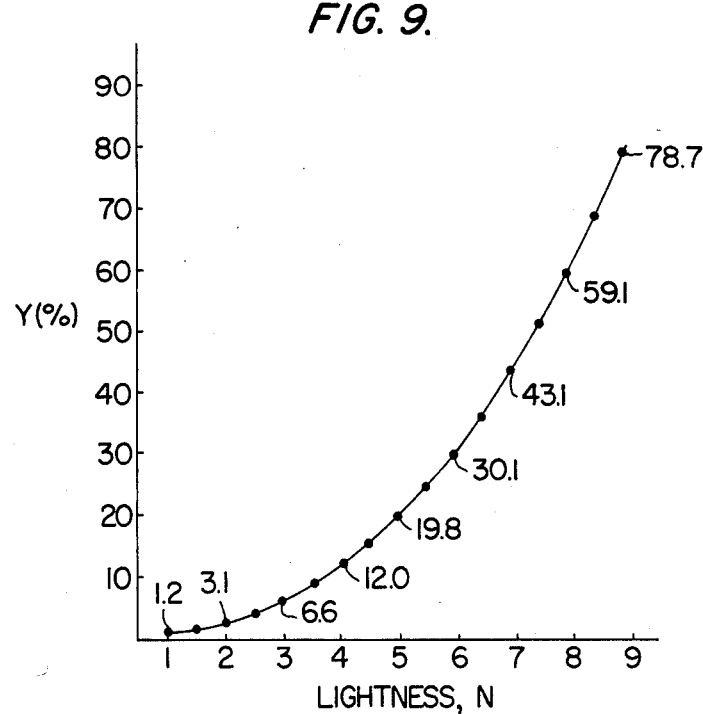
FIG. 9 is a curve showing the relation between the lightness N of a surface and the corresponding excitation values Y.

The lightness coefficient is generally determined from N/Y which is the result of calculations made on the basis of the known relation between the lightness N and the Y factor of tristimulus values and which is shown in FIG. 9. In case of, for example, certain types of paint-coated surfaces, the notation N alone is preferably be used as the lightness coefficient.

(4) The formulae for determining a value representing the degree of luster of a surface according to the present invention will now be described.

Let $A_1$ be a lower limit grade G on the chart scale at which the black lines In the longitudinal chart scale member reflected in an object surface do not have an inconstant thickness, $A_2$ the lower limit grade G on the chart scale at which the black lines on the lateral chart scale reflected in an object surface do not have an inconstant thickness, $B_1$ the lower limit grade G on the chart scale at which the black lines on the longitudinal chart scale member reflected on an object surface can be recognized, $B_2$ the lower limit grade G on the chart scale at which the black lines on the lateral chart scale member reflected on an object surface can be recognized, then $A_1+A_2$ or $(A_1+A_2)/2$ is the gloss value, $B_1+B_2$ or $(B_1+B_2)/2$ is the clarity value, and N/Y or N is the lightness coefficient of the black lines. The value of the luster of an object surface is obtained by multiplying the sum of the value of the gloss thereof and the value of the clarity thereof by the lightness coefficient of the black lines on the chart scale. These values and coefficient are suitably determined in the apparatus of FIG. 4 and using the chart scales of FIG. 3 and FIG. 8 for a sample being examined.

Figures 2, 5:
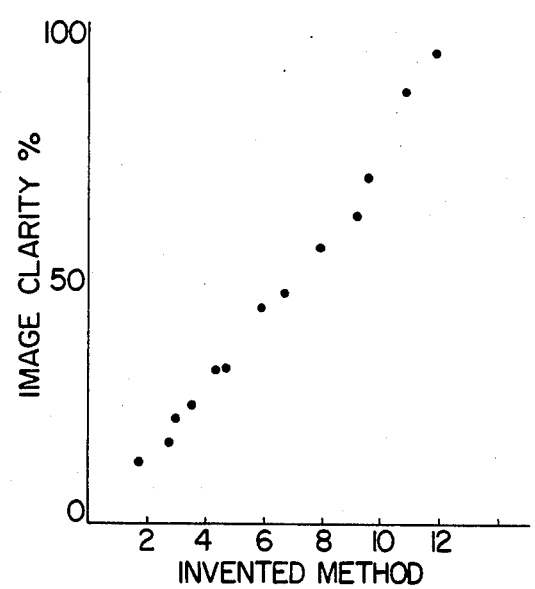

The effect of the present invention will now be described. FIG. 5-1 is a graph showing the relation between the values of the image reflecting capability of a surface which are determined by the JISH 8686 method, and which are along the longitudinal axis, and the values of the luster of the surface, which are determined by a conventional method using the apparatus and means shown in FIGS. 1 and 2, and which are along the lateral axis. There is no orderly correlation between these two kinds of values; the dots in this graph are scattered greatly. On the other hand, as shown in FIG. 5-2, a graph in which the values of the luster of a surface which are determined by the method according to the present invention are along the lateral axis, shows the orderly correlation between the values of the image reflecting capability of the surface and those of the luster thereof as compared with the similar correlation determined by using a conventional method. In the lower region of the values of the luster of a surface which are determined by the method according to the present invention, the above two kinds of values have a substantially linear correlation. In the higher region of the values of the luster of a surface which are determined by the method according to the present invention, the values determined by the JIS method are high. This indicates that the values determined by the method according to the present invention and in the high region thereof are closer to the visually-determined values rather than to the values determined by the JIS method. This effect is obtained by the rational steps which have already been described and which are used in the present invention. In these steps, the apparatus in use is formed rationally by eliminating therefrom factors which cause an optical error during the operations for determining the degrees of the gloss and visibility of an object surface, which constitute the factors of the luster thereof, and the value of the luster of an object surface is determined by additionally using a lightness coefficient. Table 1 shows the numerical values indicated in the graphs of FIG. 5.

The price of the apparatus used in the luster rating method according to the present invention is so low (about $40) that it does not pose any problems. On the other hand, the apparatus used in the JIS method to determine the image reflecting capability of a surface costs not less than $4000. In view of the apparatus cost, it is clear that the present invention has a very great advantage.

The present invention is not, of course, limited to the above embodiment; it may be modified in various ways within the scope of the appended claims.

What is claimed is:

1. A method of determining the luster of a surface as a numerical value, comprising:

projecting light from a light source through a light diffusing means and through a layer of semi-transparent material having thereon sets of spaced parallel opaque lines for projecting the lines of the sets onto the surface of a sample, the luster of which is to be determined, the thicknesses of the lines in the successive sets being reduced and the successive sets having an assigned numerical value;

viewing with the eyes the sets of lines this projected onto the surface of the sample and determining in which of the sets the lines first appear to have a wavy edge along the spaces between the lines in the set as compared to the lines which appear to have straight edges in the adjacent set having larger lines, and then choosing the numerical value assigned to sid adjacent set as the value of the degree of gloss of the surface, and then determining in which of the sets the lines first appear to run together as compared to the lines which appear to be separate in the adjacent set having larger lines, and then choosing the numerical value assigned to said lastmentioned adjacent set as the value of the degree of clarity of the surface;

visually comparing the surface with a scale of predetermined lightness values having preassigned numerical values for determining the closest lightness value, and obtaining a lightness coefficient from said lightness value; and multiplying the sum of said gloss value and said clarity value by said lightness coefficient for obtaining a numerical value for the luster of the surface of the sample.

2. A method as claimed in claim 1, in which there are two groups of sets of lines, the lines in each set being straight and the sets in each group lying side by side in a direction transverse to the length of the lines and the two groups extending perpendicular to each other, and the method comprises carrying out the steps of viewing, determining the respective sets and choosing the assigned numerical values for the sets of lines in both groups and then averaging the values of the degree of gloss and the values of the degree of clarity for obtaining average values thereof, and using said average values in said multiplying step.

3. A method as claimed in claim 2 in which the thicknesses of the lines in successive sets decrease arithmetically.

4. A method as claimed in claim 2 in which the thicknesses of the lines in successive sets decrease geometrically.

* * * * *